United States Patent [19]
Jackanicz et al.

[11] Patent Number: 5,869,081
[45] Date of Patent: Feb. 9, 1999

[54] PROGESTERONE VAGINAL RING FOR TREATMENT OF INFERTILITY

[75] Inventors: Theodore Jackanicz, New York, N.Y.; Horacio B. Croxatto Avoni, Santiago, Chile; Leopoldo Glasser Drexler, Santiago, Chile; Fernando Zegers-Hochschild, Santiago, Chile

[73] Assignee: The Population Council, New York, N.Y.

[21] Appl. No.: 672,436

[22] Filed: Jun. 28, 1996

[51] Int. Cl.$^6$ .............................. A61F 6/08; A61K 31/56; C07J 1/00
[52] U.S. Cl. ........................ 424/432; 424/430; 514/177; 514/805; 514/899; 514/964; 514/967; 552/502
[58] Field of Search ................................ 424/432, 430; 552/539, 595, 607, 502; 514/805, 899, 177, 967, 964

[56] References Cited

U.S. PATENT DOCUMENTS

| | | |
|---|---|---|
| 4,816,257 | 3/1989 | Buster et al. . |
| 5,543,150 | 8/1996 | Bologna et al. . |

OTHER PUBLICATIONS

Diaz et al. (1985) *Contraception* 32:603.
Landgren et al. (1995) *Contraception* 45:343.
Landgren et al. (1995) *Contraception* 51:255.
Simon et al. (1986) *Fertility and Sterility* 46:619.
Ahren et al. (1983) *Contraception* 28:315.
Croxatto et al. "Progesterone vaginal rings for contraception during breastfeeding" in *Female Contraception and Male Fertility Regulation*, Runnebaum et al, eds. Parthenon Publishing, Casterton Hall, U.K., 1992, 135–142.
Diaz et al. (1985) *Contraception* 32:603.
Diaz et al. (1991) *Ann. New York Acad. Sci.* 626:11.
Matlin et al. (1992) *Contraception* 45:329.
Miles et al. (1994) *Fertil. Steril.* 62:485.
Sauer et al. (1987) *Hum. Reprod.* 2:287.
Smitz et al. (1992) *Hum. Reprod.* 7:168.
Victor et al. (1978) *Fertil. Steril.* 30:631.
WHO Special Programme of Research, Development and Research Training in Human Reproduction (1979) *J. Steroid Biochem.* 11:461.

*Primary Examiner*—David Saunders
*Assistant Examiner*—F. Pierre VanderVegt
*Attorney, Agent, or Firm*—Lerner, David, Littenberg, Krumholz & Mentlik

[57] ABSTRACT

The present invention relates to a method of administering progesterone to a normogonadal or a functionally agonadal human female undergoing an assisted reproduction technique. The invention further provides a method of hormone replacement for a human female. In a preferred embodiment of the present invention, progesterone is provided by intravaginal administration of a progesterone-containing polysiloxane ring.

18 Claims, 1 Drawing Sheet ns for endometrial priming in functionally agonadal women. The ring and cylinder system was used to achieve serum levels of 17β-estradiol and progesterone within the normal range for an entire menstrual cycle. U.S. Pat. No. 4,816,257 discloses the use of polysiloxane rings containing 17β-estradiol or 17β-estradiol and progesterone to mimic normal steroid hormone levels in a functionally agonadal human female. To stimulate a normal human menstrual cycle, a sequence of rings and tampons of different formulations was required. Ring I, containing 200 mg 17β-estradiol, was administered intravaginally on day one, and removed and replaced by Ring II, containing 400 mg 17β-estradiol on day fourteen. On day nineteen, Ring III, containing 400 mg 17β-estradiol and 1000 mg progesterone, was substituted for Ring II. One day twenty-five, Ring I was substituted for Ring III. On days fifteen to twenty-eight, a polysiloxane tampon containing 2000 mg progesterone was added to the regimen. Accordingly, the use of intravaginal rings to stimulate a normal menstrual cycle as disclosed by U.S. Pat. No. 4,816,257 is complex and inconvenient.

PROGESTERONE VAGINAL RING FOR TREATMENT OF INFERTILITY

FIELD OF THE INVENTION

Assisted reproduction techniques such as in vitro fertilization and embryo transfer generally require progesterone supplementation to prepare the endometrium for implantation and to maintain pregnancy, particularly after oocyte donation in a functionally agonadal female. The present invention is directed to the use of intravaginal rings for the administration of progesterone to establish and maintain pregnancy in such cases, including the functionally agonadal human female.

BACKGROUND OF THE INVENTION

Assisted reproduction techniques include in vitro fertilization (IVF) and embryo transfer (ET). In IVF-ET, an oocyte is surgically removed, fertilized in vitro, and placed in the uterus or Fallopian tube of the same woman. In oocyte donation, the oocyte is recovered from a donor and after IVF it is transferred to an infertile recipient as in ET. This procedure requires synchronization between the donor and the recipient, which is generally achieved by administering steroid hormones to the recipient.

In regular IVF-ET, the treatments given to induce multiple follicle growth often lead to insufficient luteal function. Therefore progesterone supplementation is required for implantation and initial maintenance of pregnancy. OD-IVF-ET is performed in functionally agonadal females and thus there is no source of endogenous progesterone until the eighth to tenth week of pregnancy when the placenta assumes this function. Thus, progesterone supplementation is always required in OD-IVF-ET, and is required for longer periods of time.

Thus, exogenous progesterone supplementation is well-established in IVF and ET, as well as in the treatment of other ovulatory dysfunction. In addition, exogenous progesterone is an essential part of the hormonal replacement therapy required by the agonadal women to maintain pregnancy after oocyte donation.

The prior art methods of administration of exogenous progesterone to women undergoing assisted reproduction techniques suffer from significant disadvantages. Oral administration of progesterone is ineffective due to rapid clearance by the liver, resulting in low bioavailability in the circulation. Intramuscular administration is the most widely used form of progesterone replacement in agonadal women undergoing oocyte donation. This route, however, requires daily administration of high doses of progesterone (50 to 100 mg/day) for up to 100 days. The high serum concentration of progesterone and daily i.m. injections produce severe patient discomfort. Intravaginal progesterone administration has been used to prepare the endometrium for implantation, but may require insertion of progesterone tablets or suppositories into the vagina twice a day for approximately one hundred days.

Polysiloxane carriers have been used for delivery of progesterone as a contraceptive for lactating women (Croxatto et al., 1991, in "Female Contraception and Male Fertility Regulation. Advances in Gynecological and Obstetric Research Series", Reinnebaum et al., eds.) and for delivery of estradiol in postmenopausal women (Stumpf et al. (1982), *J. Clin. Endocrinol. Metab.*, 58:208).

Simon et al. (1986), *Fertility and Sterility*, 46:619 disclose 17β-estradiol and/or progesterone-impregnated polysiloxane vaginal rings and cylinders for endometrial priming in functionally agonadal women. The ring and cylinder system was used to achieve serum levels of 17β-estradiol and progesterone within the normal range for an entire menstrual cycle. U.S. Pat. No. 4,816,257 discloses the use of polysiloxane rings containing 17β-estradiol or 17β-estradiol and progesterone to mimic normal steroid hormone levels in a functionally agonadal human female. To stimulate a normal human menstrual cycle, a sequence of rings and tampons of different formulations was required. Ring I, containing 200 mg 17β-estradiol, was administered intravaginally on day one, and removed and replaced by Ring II, containing 400 mg 17β-estradiol on day fourteen. On day nineteen, Ring III, containing 400 mg 17β-estradiol and 1000 mg progesterone, was substituted for Ring II. One day twenty-five, Ring I was substituted for Ring III. On days fifteen to twenty-eight, a polysiloxane tampon containing 2000 mg progesterone was added to the regimen. Accordingly, the use of intravaginal rings to stimulate a normal menstrual cycle as disclosed by U.S. Pat. No. 4,816,257 is complex and inconvenient.

The present invention overcomes the deficiencies of the prior art by providing a convenient and efficient method of administering progesterone to a functionally agonadal human female undergoing assisted reproduction.

SUMMARY OF THE INVENTION

The present invention provides a method of administering progesterone for the establishment and maintenance of pregnancy in a functionally agonadal human female. The method of the invention comprises inserting a carrier containing progesterone into the vagina of the functionally agonadal female and maintaining the carrier intravaginally for about twenty-eight days. In a preferred embodiment, the carrier is a polysiloxane ring having an in vitro release rate from about 5 to about 15 mg progesterone/day.

The present invention further provides a method of hormone replacement therapy for a functionally agonadal human female undergoing assisted reproduction. The method comprises inserting a carrier containing progesterone into the vagina of a functionally agonadal human female and maintaining the carrier intravaginally until about the seventh to twelfth week of pregnancy. In a preferred embodiment, the carrier is a polysiloxane ring having an in vitro release rate of from about 5 to about 15 mg progesterone/day.

DETAILED DESCRIPTION OF THE INVENTION

Figure 1:
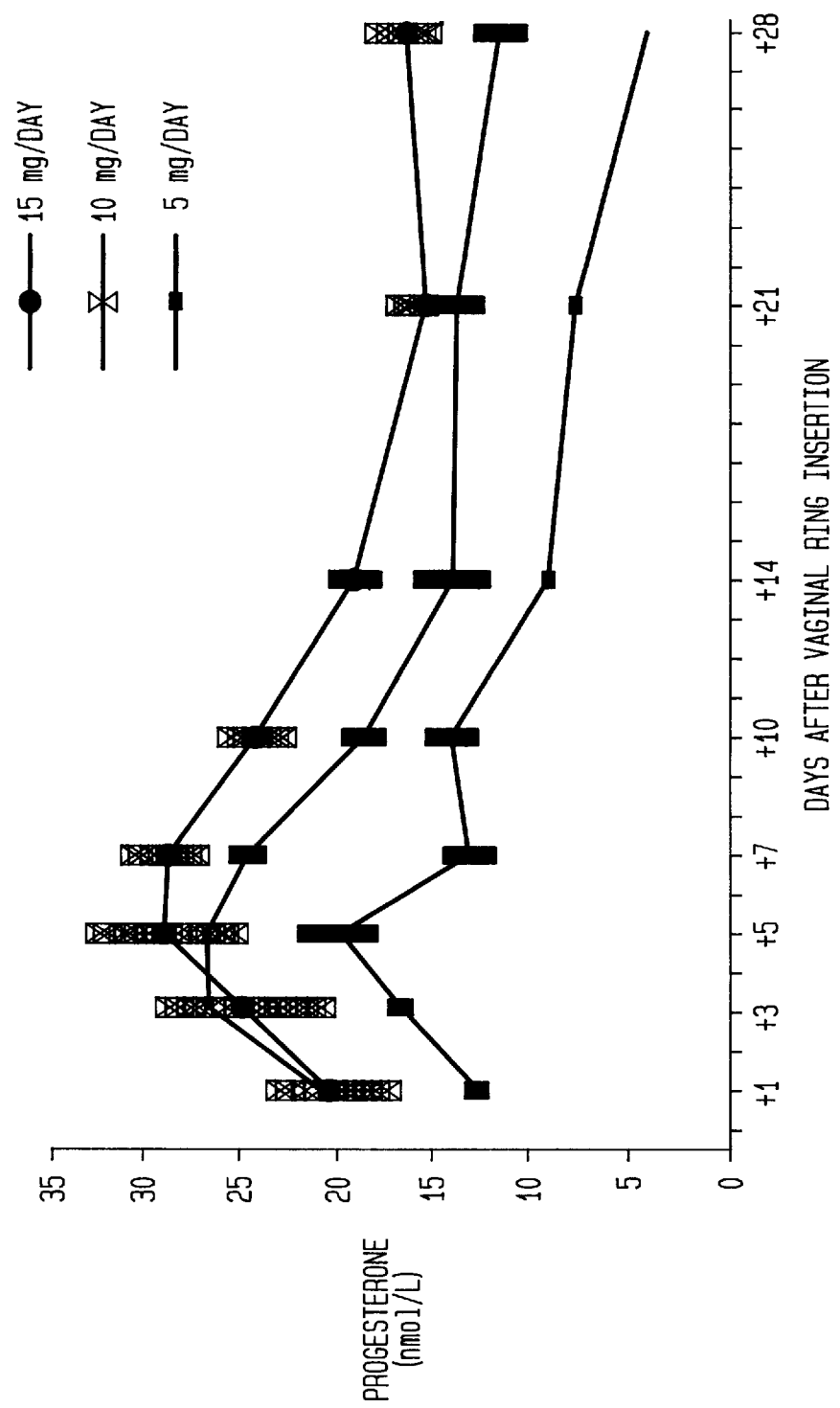
FIG. 1 is a graph of the mean ±SE plasma progesterone levels (nmol/L) from day +1 of vaginal ring insertion.

The present invention relates to methods for administering progesterone to women with functioning ovaries and to functionally agonadal women. Women with functioning ovaries who are infertile or cannot conceive because their partner is infertile can become pregnant through assisted reproduction techniques. However, the hormonal treatments used to induce multiple follicle growth cause insufficient production of progesterone by the corpus luteum. Thus progesterone supplementation is necessary to prepare the endometrium to initiate and maintain implantation. Functionally agonadal women are infertile as a result of undeveloped or improperly developed ovaries, surgical removal of ovaries, or other ovarian failure or dysfunction. Assisted reproduction techniques such as OD, IVF and ET allow functionally agonadal women to become pregnant. However, hormone supplementation is necessary in assisted reproduction techniques in order to prepare the endometrium for the establishment and continuation of pregnancy.

It has been discovered in accordance with the present invention that intrauterine progesterone levels sufficient to exert an adequate progestational effect in the endometrium for establishment and maintenance of pregnancy can be achieved in a simple and convenient manner. In particular, intravaginal administration of a physiologically acceptable carrier having an in vitro release rate of from about 5 to about 15 mg progesterone results in an adequate progestational effect on the endometrium. Prior art methods have sought to deliver progesterone and estrogen in a manner that mimics the serum levels of a normal menstrual cycle, and thus require multiple administrations of varying dosages of progesterone and estrogen over a monthly cycle. In contrast, in accordance with the present invention, it has been found that intravaginal delivery of progesterone that results in low circulatory levels (e.g., 12–15 nmol/L) has an adequate biological effect on the endometrium. Further, such intravaginal carriers having in vitro release rates of 5 to about 15 mg progesterone per day are capable of maintaining these levels for at least twenty-eight days. Accordingly, the present method is safe in that no systemic side effects are produced by the very low circulatory levels of progesterone. In addition, the present method is convenient because a maximum of one intravaginal administration of progesterone in the first month and another at the beginning of the second month by the present method is sufficient for the establishment and maintenance of pregnancy.

The present invention provides a method of administering progesterone for the establishment and maintenance of pregnancy by assisted reproduction techniques in a normogonadal and in a functionally agonadal human female. The method comprises inserting a progesterone-containing carrier into the vagina of a normogonadal or a functionally agonadal human female and maintaining the carrier intravaginally for at least about twenty-eight days.

The present invention also provides a method of hormone replacement therapy for a human female undergoing assisted reproduction. The method comprises inserting a progesterone-containing carrier into the vagina of a human female undergoing assisted reproduction and maintaining the carrier intravaginally until about the seventh to twelfth week of pregnancy.

The physiologically acceptable progesterone-containing carriers of the present invention are preferably ring-shaped solid carriers made of silicone rubber, also referred to herein as polysiloxane, or other suitable material. Delivery of steroid hormones by polysiloxane vagina rings is known in the art. The rate of passage of progesterone from a polysiloxane ring is dependent upon factors including the surface area of the ring. Accordingly, the amount of progesterone in the ring is conveniently described in terms of the in vitro release rate of progesterone from the ring. In vitro release rates are routinely used in the art to characterize hormone-containing polysiloxane rings. For example, polysiloxane rings having an external diameter of 60 mm and a cross section of 9 mm and containing 0.5, 1.0 or 2.0 grams of progesterone homogeneously dispersed have in vitro release rates of about 5, 10 or 15 mg of progesterone per day, respectively. Progesterone-containing polysiloxane rings for intravaginal administration are commercially available, and may be made by methods well-known in the art. Progesterone-containing polysiloxane rings having in vitro release rates of from about 3 to about 20 mg of progesterone per day are contemplated for use in the present method. In a preferred embodiment the polysiloxane rings have an in vitro release rate of from about 5 to about 15 mg of progesterone per day. In a most preferred embodiment the polysiloxane rings have an in vitro release rate of about 10 mg of progesterone per day. In another preferred embodiment, the 10 mg ring is replaced by a ring having an in vitro release rate of 15 mg per day upon documentation of pregnancy.

The progesterone-containing polysiloxane carriers are administered by insertion into the vagina. The rings are inserted into the vagina and positioned around the cervix. The ring can be inserted and removed by the female subject in a manner similar to that of the commonly used diaphragm, thus providing yet another advantage of the present invention.

The progesterone-containing carrier may be administered about two to seven days, and preferably three days, before embryo transfer, and may be supplemented by other hormone administration, for example oral administration of estradiol-17β. In a preferred embodiment the carrier is a ring and is inserted three days before embryo transfer. The ring preferably has an in vitro release rate of 10 mg of progesterone per day. The carrier is removed and replaced by another carrier after about twenty-eight days. Alternately, a 10 mg ring may be replaced upon documentation of pregnancy by a 15 mg ring. If pregnancy occurs, the carrier allows sufficient progesterone for the maintenance of pregnancy until the luteal-placental shift, at which time administration may be discontinued. In a preferred embodiment, the 15 mg ring is maintained continuously in the vagina, and administration is discontinued at about the twelfth week of pregnancy.

The invention is further illustrated by the following specific examples, which are not intended in any way to limit the scope of the invention.

EXAMPLE I

A pharmacodynamic study was conducted in eight women with premature ovarian failure. All subjects were amenorrheic with high follicle stimulating hormone (FSH) and low estradiol, and were willing to participate in an oocyte donation program. Endometrial proliferation was induced with a fixed oral dose of 6 mg/day micronized estradiol-17β ($E_2$) until the endometrium reached eight to ten millimeters. At this point (day 0) a silicone rubber vaginal ring (Laboratorio Silesia, Santiago, Chile) with an external diameter of 60 mm and cross section of 9 mm was placed in the vagina while continuing $E_2$ supplementation. The vaginal rings contained either 0.5, 1 or 2 grams of the natural hormone progesterone homogeneously dispersed and had in vitro release rates of 5, 10 or 15 mg of progesterone per day, respectively. Two women used the 5 mg vaginal ring, while three patients were assigned to each of the other two doses. Ten ml of blood was obtained from the antecubital vein on the morning of vaginal ring insertion, the morning after, every other day until day ten, and weekly until day twenty-eight. Plasma was stored for measurement of progesterone and $E_2$ by enzyme immunoassay by the Enzymum Test System ES-300 (Boehringer Mannheim GmbH).

Plasma progesterone concentrations prior to inserting the vaginal ring ranged from 0.1 to 0.7 nmol/L. Twenty-four hours after inserting the ring, the mean (±S.E.) concentration increased to 12.7±0.49, 20.7±2.09 and 19.9±3.30 nmol/L for vaginal rings with an in vitro release rate of 5, 10 and 15 mg per 24 hours, respectively. This concentration remained fairly stable during the first twenty-eight days. Repeated Measures Analysis of Variance and multiple comparisons were performed by contrast to values obtained at seven day intervals. There were no significant variations in progesterone concentration throughout the study period with the vaginal ring releasing 10 mg per 24 hours.

No differences were found in plasma progesterone when comparing the 10 and 15 mg vaginal rings, although these values were significantly higher as compared to the 5 mg vaginal ring ($p>0.05$), as shown in FIG. 1.

Endometrial biopsies were performed with an endometrial suction curette (Z-Sampler, California) on day +3 in six patients. Three patients using the 10 mg vaginal ring had endometrial biopsies repeated on day +7. Endometrial dating criteria as described by Noyes et al. (1950) *Fertil. Steril.* 1:3–25 was used for assessing the day of the menstrual cycle. Endometrial tissue was processed routinely to obtain hematoxylin and eosin stained sections. These were coded and examined by the same pathologist, who was blinded for the hormone replacement therapy of each patient.

On day +3, surface epithelium appeared cylindrical, without mitosis or cilia. The endometrial glands were tubular in shape, rounded or oval, and contained scanty secretions. The epithelium was cylindrical and presented occasional mitotic figures. Glandular epithelium contained abundant infranuclear vacuoles. The stroma presented irregular edema, more intense near the surface epithelium. There was neither mitosis nor inflammatory reaction.

On day +7 there were no signs of trauma or inflammation caused by the previous biopsy. The glands were tortious with some degree of dilation. The lumen was full of an intensely eosinophilic homogeneous secretion. The epithelium presented vacuolization in the supranuclear portion of the cytoplasm, and no mitosis was found. The stroma presented incipient or confluent perivascular decidual reaction. Other parts were edematous with no inflammatory reaction.

This example demonstrates that sustained release of progesterone by a vaginal ring results in low circulatory levels of the hormone, while concentrating its biological effect at a regional level. In particular, plasma progesterone as low as 10 to 15 nmol/L was associated with progestational effects on the endometorum and accelerated decidualization. This advanced endometrium was observed both on days +3 an +7. According to histologic observations, the appearance of endometrial tissues obtained on day +3 corresponded to day +4–6 of a spontaneous ovulatory cycle. Endometrial tissue obtained by the same methodology from women supplemented with intramuscular progesterone did not exhibit this advanced pattern.

EXAMPLE II

During pregnancy cycles, six subjects from Example I all received the same hormone replacement therapy. Progesterone was supplemented with a vaginal ring having an in vitro release rate of 10 mg per 24 hrs. The ring was inserted three days before two to four embryos at the two to four cell stage were transferred to the uterine cavity. Ten ml of blood was obtained from this group between days +12 and +18. The mean ±S.D. of plasma progesterone on days +12 to +18 was 15.7±0.31. This valve does not differ significantly from the value found in the same patients found in the study cycle of Example I, 15.9±1.39.

In three out of the six pregnancy cycles, a uterine fluid sample was taken prior to embryo transfer. An empty catheter was inserted in the uterine cavity through a fine canula placed along the cervical canal in order to avoid contamination with cervical mucus. Approximately 10 ml of fluid was gently aspirated from the uterine cavity. The catheter was flushed with 300 ml of buffer (pH 7), and progesterone was measured as described in Example I. One woman supplemented with a daily i.m. injection of 100 mg of progesterone (the routine hormone replacement therapy for oocyte donation) served as a control for uterine fluid progesterone concentration.

Because the procedure was performed immediately prior to embryo transfer, aspiration was short and minimal, and sufficient fluid was obtained in only three cases. Intrauterine progesterone was 60, 72 and 107 nmol/L compared to a mean of 27.5 nmol/L in peripheral circulation. In the woman receiving daily 100 mg i.m. injections, circulatory levels of progesterone exceeded 100 nmol/L, while the concentration in uterine fluid was only 42 nmol/L.

This example demonstrates that high uterine concentration of progesterone and low peripheral concentrations can be achieved by using a progesterone-containing intravaginal ring. Roblero et al. (1976) *J. Reprod. Fertil* 46:475 report that rat embryos at the two cell stage cultured in vitro in the presence of progesterone exhibit better development to the blastocyst stage than those cultured in the absence of hormone. These studies suggest that high uterine concentrations of progesterone facilitate blastocyst formation and, therefore, implantation.

EXAMPLE III

Seventeen functionally agonadal women used a progesterone containing vaginal ring having an in vitro release rate of 10 mg per day as the only source of progesterone during an oocyte donation cycle. When pregnancy was documented on day 12 after embryo transfer, the 10 mg ring was replaced by a vaginal ring having an in vitro release rate of 15 mg, which was left in place until the twelfth week of pregnancy. In the same period of time eighteen other women received daily i.m. injections of 100 mg progesterone. The decision to use one or the other route of administration was not randomized. All other parameters were comparable, including the mean number of embryos transferred (3.5 and 3.7, respectively). In every treatment cycle at least half of the concepti transferred were considered to be of good quality. The age distribution of donors was comparable, with the median in the age interval of 30 to 34 years for both groups of donors.

The clinical pregnancy rate was 52.9% in the group using the vaginal ring and 38.9% in the group receiving daily injections. The nidation rate (total number of gestational sacs/total number of embryos transferred) in women using vaginal rings was 23.7% (14/59) compared to 13.6% (9/66) in women receiving i.m. progesterone.

This example demonstrates that the vaginal ring is comparable to or better than daily i.m. progesterone administration in terms of nidation and overall pregnancy rates.

EXAMPLE IV

Forty-nine normogonadal women undergoing IVF-ET were randomly assigned to receive a progesterone containing vaginal ring having an in vitro release rate of 10 mg per day (n=23) or a daily intramuscular (i.m.) injection of 50 mg progesterone (n=26). In order to induce multiple follicle growth, subjects received a sequential treatment with a gonadotropin releasing hormone (GnRH) agonist, human menopausal gonadotropin (hMG) and human chronic gonadotropin (hCG). Oocytes were aspirated thirty-six hours after administering hCG, and treatment with progesterone, either i.m. or by vaginal ring, began at this time. Progesterone treatment continued for a maximum of seven weeks. The clinical pregnancy rates were 30.4% (7/23) for the group treated by intravaginal ring and 38.4% (10/26) in the group treated by i.m. injection. This example demonstrates that progesterone supplementation via the intravaginal ring is as effective as daily i.m. injections, but far more comfortable for the patient.

We claim:

1. A method of progesterone supplementation to prepare the endometrium for embryo implantation and to maintain pregnancy in a normogonadal or a functionally agonadal human female comprising administering progesterone intravaginally to said normogonadal or functionally agonadal human female, in amounts that are effective to establish a serum level of progesterone between 10 and 15 nmol/L that is effective to exert a progestational effect in the endometrium, for at least about twenty-eight days.

2. The method of claim 1 wherein, upon documentation of pregnancy, said progesterone administration continues until the twelfth week of pregnancy.

3. A method of progesterone supplementation to prepare the endometrium for embryo implantation and to maintain pregnancy in a human female comprising inserting a first progesterone-containing polysiloxane ring having an in vitro release rate of 10 milligrams of progesterone per day into the vagina of a functionally agonadal adult human female about three days before embryo transfer, replacing said ring by a second progesterone-containing polysiloxane ring having an in vitro release rate of 15 milligrams of progesterone per day upon documentation of pregnancy, and leaving said second ring in place until about the twelfth week of pregnancy.

4. A method of hormone supplementation for a human female comprising administering progesterone intravaginally to said female in amounts that are effective to establish a serum level of progesterone between 10 and 15 nmol/L that is effective to exert a progestational effect in the endometrium, wherein upon documentation of pregnancy progesterone administration continues until the seventh to twelfth week pregnancy.

5. The method of claim 1, wherein, upon documentation of pregnancy, said progesterone administration continues until the twelfth week of pregnancy.

6. The method of claim 1, wherein said progesterone is administered intravaginally by inserting a progesterone-containing polysiloxane ring into the vagina of the female.

7. The method of claim 6, wherein said polysiloxane ring has an in vitro release rate of about 5 to about 15 milligrams of progesterone per day.

8. The method of claim 7, wherein said polysiloxane ring has an vitro release rate of about 10 milligrams of progesterone per day.

9. The method of claim 6, wherein said polysiloxane ring is a first polysiloxane ring and said method further comprises the step of removing said first ring from the vagina after about 28 days and inserting a second progesterone-containing polysiloxane ring into the vagina, the administration of which, upon documentation of pregnancy, continues until the twelfth week of pregnancy.

10. The method of claim 1, wherein said progesterone is administered in amounts that are effective to establish for at least 28 days a serum level of progesterone between about 12 and about 15 nmol/L.

11. The method of claim 4, wherein said progesterone administration continues until the twelfth week of pregnancy.

12. The method of claim 4, wherein said progesterone is administered intravaginally by inserting a progesterone-containing polysiloxane ring into the vagina of the female.

13. The method of claim 12, wherein said polysiloxane ring has an in vitro release rate of about 5 to 15 milligrams of progesterone per day.

14. The method of claim 13, wherein said polysiloxane ring has an in vitro release rate of about 10 milligrams of progesterone per day.

15. The method of claim 4, wherein said progesterone is administered in amounts that are effective to establish for at least 28 days a serum level of progesterone between about 12 and about 15 nmol/L.

16. A method of hormone supplementation for a human female comprising administrating progesterone intravaginally to said female at in vitro release, rates of from about 5 to about 15 mg/day that is effective to exert a progestational effect in the endometrium, for at least about 28 days.

17. The method of claim 16 wherein said progesterone is administered intravaginally by inserting a progesterone-containing polysiloxane ring into the vagina of the female.

18. The method of claim 16 wherein said polysiloxane ring is a first polysiloxane ring and said method further comprises the step of removing said first ring from the vagina after about 28 days and inserting a second progesterone-containing polysiloxane ring into the vagina, the administration of which, upon documentation of pregnancy continues until the twelfth week of pregnancy.

* * * * *

UNITED STATES PATENT AND TRADEMARK OFFICE
CERTIFICATE OF CORRECTION

PATENT NO. : 5,869,081
DATED : February 9, 1999
INVENTOR(S) : Jackanicz et al.

It is certified that error appears in the above-identified patent and that said Letters Patent is hereby corrected as shown below:

Column 8, line 2, after "has an" insert --in--.

Column 8, line 20, "intavaginally" should read --intravaginally".

Column 8, line 34, "release." should read --release--.

Signed and Sealed this

Twenty-ninth Day of June, 1999

Attest:

Q. TODD DICKINSON

*Attesting Officer*  Acting Commissioner of Patents and Trademarks